United States Patent
Toyama et al.

(10) Patent No.: US 10,302,776 B2
(45) Date of Patent: May 28, 2019

(54) SCINTILLATOR PANEL AND RADIATION DETECTOR

(71) Applicant: HAMAMATSU PHOTONICS K.K., Hamamatsu-shi, Shizuoka (JP)

(72) Inventors: Shintaro Toyama, Hamamatsu (JP); Yutaka Kusuyama, Hamamatsu (JP); Masanori Yamashita, Hamamatsu (JP); Hirotake Osawa, Hamamatsu (JP); Hidenori Jonishi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 16/061,385

(22) PCT Filed: Nov. 29, 2016

(86) PCT No.: PCT/JP2016/085342
§ 371 (c)(1),
(2) Date: Jun. 12, 2018

(87) PCT Pub. No.: WO2017/104400
PCT Pub. Date: Jun. 22, 2017

(65) Prior Publication Data
US 2019/0041532 A1 Feb. 7, 2019

(30) Foreign Application Priority Data
Dec. 14, 2015 (JP) .................................. 2015-243188

(51) Int. Cl.
*G01T 1/20* (2006.01)
*A61B 6/00* (2006.01)
(Continued)

(52) U.S. Cl.
CPC .............. *G01T 1/2023* (2013.01); *A61B 6/00* (2013.01); *G01T 1/20* (2013.01); *G01T 1/2002* (2013.01); *G01T 1/2018* (2013.01); *G21K 4/00* (2013.01)

(58) Field of Classification Search
CPC ... G01T 1/2002; G01T 1/2018; G01T 1/2023; G21K 4/00
See application file for complete search history.

(56) References Cited

U.S. PATENT DOCUMENTS 7,932,499 B2 * 4/2011 Furuichi ............... G01T 1/2018
250/366
8,068,896 B2 * 11/2011 Daghighian ........... A61B 6/037
600/436
(Continued)

FOREIGN PATENT DOCUMENTS

JP H10-319126 A 12/1998
JP 2003-167060 A 6/2003
(Continued)

OTHER PUBLICATIONS

International Preliminary Report on Patentability dated Jun. 28, 2018 for PCT/JP2016/085342.

*Primary Examiner* — Mark R Gaworecki
(74) *Attorney, Agent, or Firm* — Drinker Biddle & Reath LLP

(57) ABSTRACT

A scintillator panel that converts radiation into scintillation light includes a substrate that includes a principal surface, a scintillator layer that is disposed on the principal surface, and a reflective layer that is disposed on the scintillator layer and reflects the scintillation light. The scintillator layer includes a plurality of scintillator portions which are arranged with a predetermined pitch on the principal surface. Each scintillator portion includes a side face that extends in a direction crossing the principal surface. The reflective
(Continued)

layer includes a plurality of metal particles with a foil shape extending along the side faces and is disposed so as to cover the side faces.

12 Claims, 7 Drawing Sheets

(51) Int. Cl.
*G21K 4/00* (2006.01)
*G01T 1/202* (2006.01)

(56) References Cited

U.S. PATENT DOCUMENTS

| | | | | |
|---|---|---|---|---|
| 8,350,218 | B2* | 1/2013 | Thon | G01T 1/2002 250/361 R |
| 2013/0134312 | A1* | 5/2013 | Nagano | G01T 1/2002 250/363.01 |
| 2015/0059963 | A1* | 3/2015 | Nitta | G01T 1/20 156/154 |
| 2015/0216497 | A1* | 8/2015 | Hayashi | A61B 6/566 378/62 |
| 2015/0241570 | A1* | 8/2015 | Perna | G01T 1/2002 250/366 |
| 2015/0310953 | A1* | 10/2015 | Okamura | G01T 1/2002 250/487.1 |
| 2016/0274248 | A1* | 9/2016 | Hasegawa | G02B 5/0891 |
| 2017/0199285 | A1* | 7/2017 | Adachi | A61B 6/03 |
| 2017/0269257 | A1* | 9/2017 | Scoullar | G01V 5/0041 |
| 2018/0188386 | A1* | 7/2018 | Kondo | G01T 1/1644 |
| 2018/0252824 | A1* | 9/2018 | Morimoto | A61B 6/03 |

FOREIGN PATENT DOCUMENTS

| | | |
|---|---|---|
| JP | 2004-25809 A | 1/2004 |
| JP | 2012-2627 A | 1/2012 |
| JP | 2014-59172 A | 4/2014 |
| JP | 2016-224105 A | 12/2016 |
| WO | WO-2010/092869 A1 | 8/2010 |
| WO | WO-2013/080565 A1 | 6/2013 |
| WO | WO-2014/080941 A1 | 5/2014 |

* cited by examiner

SCINTILLATOR PANEL AND RADIATION DETECTOR

TECHNICAL FIELD

An aspect of the invention relates to a scintillator panel and a radiation detector.

BACKGROUND ART

Patent Literature 1 discloses an X-ray flat panel detector. The X-ray flat panel detector includes a plurality of pixel units which are two-dimensionally arranged. Each pixel unit includes a scintillator portion. A cutoff area is formed between the scintillator portions of pixel units adjacent to each other. A reflective member that reflects visible light is disposed in the cutoff area.

CITATION LIST

Patent Literature

Patent Literature 1: Japanese Unexamined Patent Publication No. 2003-167060

SUMMARY OF INVENTION

Technical Problem

In such an X-ray flat panel detector, an improvement in resolution is achieved using an X-ray absorbing material as a material of the reflective member. In this way, there is demand for an improvement in resolution in this technical field. In order to improve a resolution, for example, disposing an absorber layer that absorbs scintillation light in the cutoff area can be considered. However, in this case, there is concern of a decrease of a light output.

An object of an aspect of the invention is to provide a scintillator panel and a radiation detector that can curb a decrease of a light output and improve a resolution.

Solution to Problem

According to an aspect of the invention, there is provided a scintillator panel that converts radiation into scintillation light, the scintillator panel including: a substrate that includes a principal surface; a scintillator layer that is disposed with a predetermined pitch on the principal surface; and a reflective layer that is disposed on the scintillator layer and reflects the scintillation light, wherein the scintillator layer includes a plurality of scintillator portions which are arranged on the principal surface, each scintillator portion includes a side face that extends in a direction crossing the principal surface, and the reflective layer includes a plurality of metal particles with a foil shape extending along the side faces and is disposed so as to cover the side faces.

In the scintillator panel, the scintillator layer includes a plurality of scintillator portions that are arranged with a predetermined pitch on the principal surface of the substrate. The reflective layer that reflects scintillation light is disposed so as to cover at least the side faces of the scintillator portions. The reflective layer includes a plurality of metal particles with a foil shape extending along the side faces of the scintillator portions. By using the reflective layer including metal particles with a foil shape in this way, it is possible to curb a decrease of a light output and to improve a resolution.

In the scintillator panel according to an aspect of the invention, an average size of the metal particles may be equal to or less than half a gap size between the side faces of the neighboring scintillator portions. In this case, the reflective layer can be formed such that the side faces of the scintillator portions are covered by easily and reliably entering the metal particles with a foil shape to the gaps between the side faces of the scintillator portions. Accordingly, it is possible to reliably curb a decrease of a light output and to improve a resolution. The average size of the metal particles with a foil shape is, for example, a value which is obtained by averaging a maximum size of a metal particle for the plurality of metal particles.

In the scintillator panel according to an aspect of the invention, the scintillator layer may be formed of a scintillator material containing CsI as a main component. In the scintillator panel according to an aspect of the invention, each scintillator portion may be formed of a single crystal of a scintillator material. Alternatively, in the scintillator panel according to an aspect of the invention, each scintillator portion may be formed of a plurality of columnar crystals of a scintillator material.

According to an aspect of the invention, there is provided a radiation detector including: a substrate that includes a principal surface and a plurality of photoelectric conversion elements formed on the principal surface; a scintillator layer that is disposed on the plurality of photoelectric conversion elements and converts radiation into scintillation light; and a reflective layer that is disposed on the scintillator layer and reflects the scintillation light, wherein the scintillator layer includes a plurality of scintillator portions which are arranged with a pixel pitch of the photoelectric conversion elements, each scintillator portion includes a side face that extends in a direction crossing the principal surface, and the reflective layer includes a plurality of metal particles with a foil shape extending along the side faces and is disposed so as to cover the side faces.

In the radiation detector, the scintillator layer includes a plurality of scintillator portions that are arranged with a pixel pitch of the photoelectric conversion elements of the substrate. The reflective layer that reflects scintillation light is disposed to cover at least the side faces of the scintillator portions. The reflective layer includes a plurality of metal particles with a foil shape that extend along the side faces of the scintillator portions. By using the reflective layer including metal particles with a foil shape in this way, it is possible to curb a decrease of a light output and to improve a resolution.

In the radiation detector according to an aspect of the invention, an average size of the metal particles may be equal to or less than half a gap size between the side faces of the neighboring scintillator portions. In this case, the reflective layer can be formed such that the side faces of the scintillator portions are covered by easily and reliably entering the metal particles with a foil shape to the gaps between the side faces of the scintillator portions. Accordingly, it is possible to reliably curb a decrease of a light output and to improve a resolution.

In the radiation detector according to an aspect of the invention, the scintillator layer may be formed of a scintillator material containing CsI as a main component. In the radiation detector according to an aspect of the invention, each scintillator portion may be formed of a single crystal of a scintillator material. Alternatively, in the radiation detector according to an aspect of the invention, each scintillator portion may be formed of a plurality of columnar crystals of a scintillator material. The scintillator layer may be formed of a scintillator material which is GOS.

Advantageous Effects of Invention

According to an aspect of the invention, it is possible to provide a scintillator panel and a radiation detector that can curb a decrease of a light output and improve a resolution.

DESCRIPTION OF EMBODIMENTS

Figure 1:
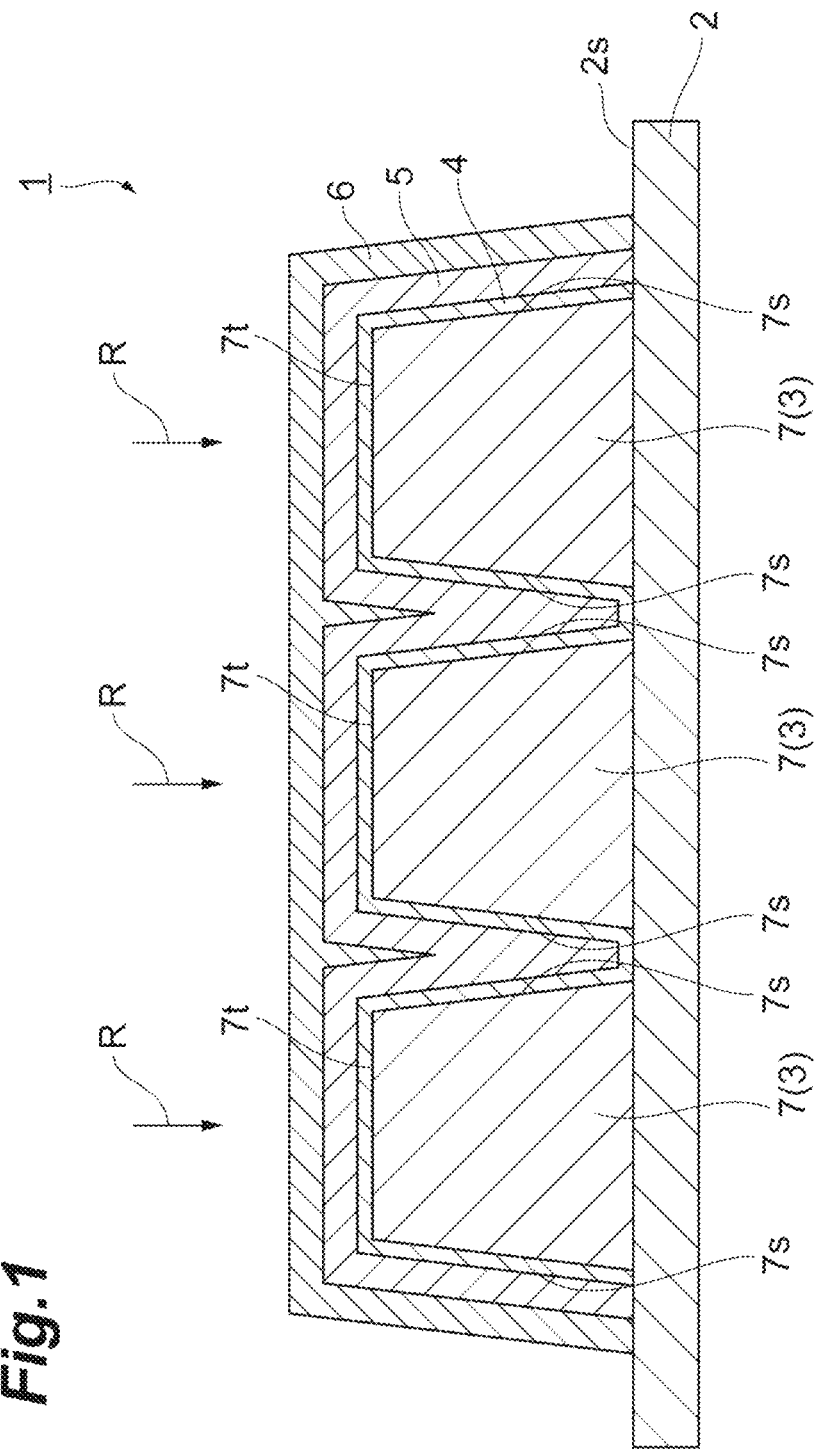
FIG. 1 is a sectional view of a scintillator panel according to an embodiment of the invention.

Hereinafter, an embodiment of an aspect of the invention will be described in detail with reference to the accompanying drawings. In the drawings, the same or corresponding elements will be referenced by the same reference signs and description thereof may not be repeated.

A scintillator panel according to an embodiment serves to convert radiation such as X-rays into scintillation light such as visible light. The scintillator panel according to the following embodiment can be used, for example, as a radiological imaging device in a mammography device, a mass chest diagnostic device, a CT device, a dental intraoral imaging device, a radiological camera, or the like.

Figure 2:
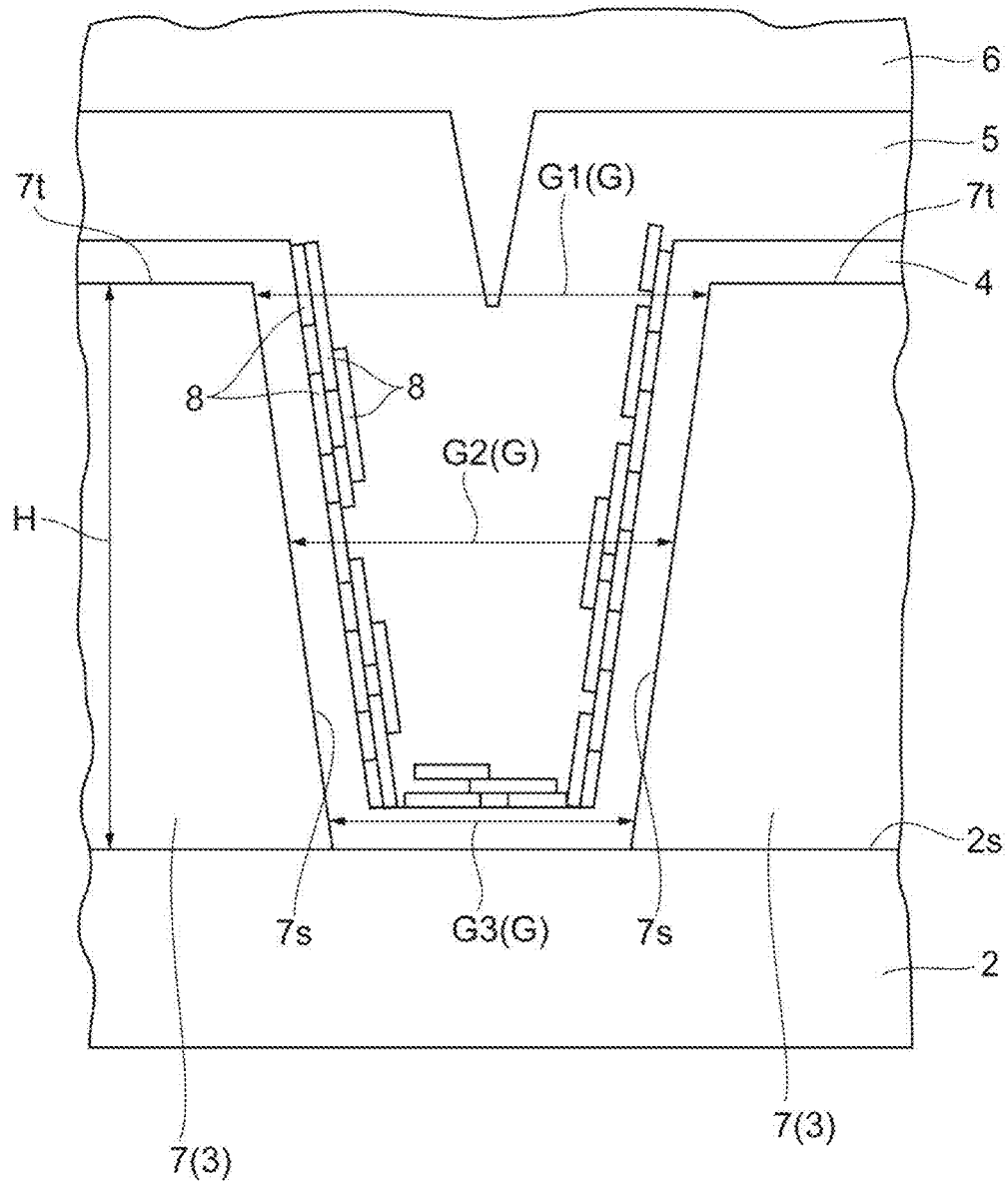
FIG. 2 is a schematic sectional view illustrating enlargement of a part of the scintillator panel illustrated in FIG. 1.

FIG. 1 is a sectional view of the scintillator panel according to this embodiment. FIG. 2 is a schematic sectional view illustrating enlargement of a part of the scintillator panel illustrated in FIG. 1. In FIG. 2, hatching of elements is not illustrated. As illustrated in FIGS. 1 and 2, the scintillator panel 1 includes a substrate 2, a scintillator layer 3, a first protective layer 4, a reflective layer 5, and a second protective layer 6.

The substrate 2 includes a principal surface 2s. The substrate 2 has, for example, a rectangular plate shape. The substrate 2 may have, for example, transmittivity of scintillation light which is generated in the scintillator layer 3. The thickness of the substrate 2 is, for example, about 2.0 mm. The substrate 2 is formed of, for example, a fiber optic plate (FOP: an optical device formed by binding a plurality of optical fibers (for example, J5734 made by Hamamatsu Photonics K.K.)).

The scintillator layer 3 generates scintillation light such as visible light in response to incidence of radiation R such as X-rays. The scintillator layer 3 is disposed on the principal surface 2s of the substrate 2. For example, the scintillator layer 3 is formed in a rectangular area of the principal surface 2s when viewed from a direction crossing (for example, perpendicular to) the principal surface 2s.

The scintillator layer 3 includes a plurality of scintillator portions 7. The scintillator portions 7 are arranged with a predetermined pitch in a two-dimensional shape on the principal surface 2s. The scintillator portions 7 are in contact with, for example, the principal surface 2s. For example, the scintillator portions 7 are not continuously connected to each other (are separated from each other). In other words, the scintillator portions 7 are formed, for example, as pixel units of an imaging sensor (that is, the scintillator layer 3 is made into pixels). The sectional shape of each scintillator portion 7 is, for example, a trapezoidal shape which is reduced as it is farther from the principal surface 2s. That is, each scintillator portion 7 has a taper shape of which a sectional area increases from the opposite side of the principal surface 2s to the principal surface 2s.

Each scintillator portion 7 is formed of, for example, a single crystal of a scintillator material. Alternatively, the scintillator portion 7 is formed of, for example, a plurality of columnar crystals of a scintillator material. Examples of the scintillator material include a material containing CsI (cesium iodide) such as CsI:Tl or CsI:Na as a main component, a material containing NaI (sodium iodide) such as NaI:Tl as a main component, $SrI_3$ (strontium iodide), $LuI_3$ (lutetium iodide), $BaF_2$ (barium fluoride), and GOS.

Each scintillator portion 7 includes side faces 7s extending in a direction (for example, a growing direction of columnar crystals) crossing the principal surface 2s. The scintillator portion 7 also includes a top face 7t that extends in a direction parallel to the principal surface 2s. The top face 7t connects the side faces 7s. A height H of the scintillator portion 7 ranges, for example, from about 150 μm to 1000 μm. The height H of the scintillator portion 7 is a distance between the top face 7t and the principal surface 2s and a thickness of the scintillator layer 3.

A gap G between the side faces 7s of the neighboring scintillator portions 7 is narrowed toward the principal surface 2s along the shape of the scintillator portions 7. In the gap G, an upper gap G1 on the top face 7t side ranges, for example, from about 5 μm to 50 μm. In the gap G, an intermediate gap G2 of an intermediate portion between the top face 7t and the principal surface 2s ranges, for example, from about 3 μm to 30 μm. In the gap G, a lower gap G3 on the principal surface 2s side ranges, for example, from about 2 μm to 15 μm. A processing pitch (for example, the predetermined pitch) of the scintillator layer 3 is, for example, about 200 μm. The processing pitch is a pitch of the gaps between the scintillator portions 7.

The first protective layer 4 is disposed on the scintillator layer 3 and the principal surface 2s of the substrate 2. The first protective layer 4 transmits radiation R. More specifically, the first protective layer 4 is disposed so as to cover the surface (the side faces 7s and the top face 7t) of each scintillator portion 7 and the principal surface 2s which is exposed from the scintillator layer 3 between the scintillator portions 7. For example, the first protective layer 4 prevents an organic solvent from invading between columnar crystals of the scintillator portions 7. A thickness T of the first protective layer 4 ranges, for example, from 1 μm to 10 μm. The first protective layer 4 is formed of, for example, parylene (polyparaxylene).

The reflective layer 5 is disposed on the scintillator layer 3 and the first protective layer 4. More specifically, the reflective layer 5 is disposed on the scintillator portions 7 with the first protective layer 4 interposed therebetween so as to cover the entire surface (the side faces 7s and the top face 7t) of each scintillator portion 7. The reflective layer 5 reflects scintillation light which is generated in the scintillator layer 3. The reflective layer 5 transmits radiation R.

The reflective layer 5 includes a plurality of metal particles 8. Accordingly, the metal particles 8 reflect scintillation light and transmits radiation R.

The metal particles 8 are disposed on the surface (the side faces 7s and the top face 7t) of each scintillator portion 7. The metal particles 8 have a foil shape (for example, a scale shape, a flake shape, or a leaf shape) that extends along the surface of the scintillator portion 7. That is, on the side faces 7s of the scintillator portion 7, the metal particles 8 extend along the side faces 7s (are arranged along the side faces 7s). The metal particles 8 overlap other metal particles 8 at least partially and come into contact therewith. Accordingly, the metal particles 8 cover the whole surface of the scintillator portion 7 with no break.

When a metal particle 8 has a foil shape, it means that the metal particle 8 does not have a spherical shape or a needle shape. More specifically, when a metal particle 8 has a foil shape, it means that, for example, when the metal particle 8 is disposed on the side face 7s, a size (a width) of the metal particle 8 along the side face 7s is larger than a size (a thickness) of the metal particle 8 in a direction crossing the side face 7s.

The average size of the metal particles 8 ranges, for example, from about 1 μm to 20 μm and may range from about 3 μm to 10 μm. Particularly, the average size of the metal particles 8 can be set, for example, to be equal to or less than half the gap G (particularly the upper gap G1) between the side faces 7s of the neighboring scintillator portions 7. When the first protective layer 4 is formed on the side faces 7s, the average size of the metal particles 8 may be set to be equal to or less than half a value which is obtained by subtracting two times the thickness of the first protective layer 4 from the gap G.

The average size of the metal particles 8 is, for example, a size which is obtained by averaging a maximum size of the metal particles 8 for a plurality of metal particles 8. The metal particles 8 are formed of, for example, Al, Ag, Au, or Pt. A particle size distribution of the metal particles 8 can be defined, for example, by a median diameter (d50) or an arithmetic average value (sum of diameters of particles/ number of particles).

The second protective layer 6 is disposed on the reflective layer 5. More specifically, the second protective layer 6 is formed on the reflective layer 5 so as to cover the scintillator layer 3, the first protective layer 4, and the reflective layer 5 as a whole. The second protective layer 6 transmits radiation R. The second protective layer 6 is formed, for example, of parylene (polyparaxylene).

An example of a method of manufacturing the scintillator panel 1 will be described below. In the manufacturing method, first, a scintillator layer is formed on the principal surface 2s by causing columnar crystals of a scintillation material to grow on the principal surface 2s of the substrate 2, for example, by a vacuum vapor deposition method. Subsequently, the scintillator layer is processed such that the scintillator layer is cut into a plurality of parts (the scintillator layer is made into pixels), for example, by irradiation with a laser beam. Accordingly, the scintillator layer 3 including a plurality of scintillator portions 7 is formed on the principal surface 2s.

Subsequently, the first protective layer 4 is formed on the scintillator layer 3 and the principal surface 2s. More specifically, the first protective layer 4 is formed so as to cover the surface (the side faces 7s and the top face 7t) of each scintillator portion 7 and the principal surface 2s which is exposed between the scintillator portions 7. Accordingly, in a subsequent step, an organic solvent is prevented from invading between the columnar crystals of the scintillator layer 3. It is possible to prevent the metal particles 8 from coming in direct contact with the scintillator layer 3. Through the above-mentioned steps, a scintillator panel including the substrate 2, the scintillator layer 3, and the first protective layer 4 is obtained.

Subsequently, the scintillator panel obtained through the above-mentioned steps is put in a vacuum vessel. In a state in which the vacuum vessel is evacuated into a vacuum, a metal paste including the metal particles 8 is applied onto the first protective layer 4. At this time, the metal paste may not fill the gaps between the side faces 7s of the scintillator portions 7. Thereafter, by opening the vacuum vessel to the atmospheric air, the gaps are filled with the metal paste using a pressure difference between the gaps between the side faces 7s and the atmospheric air. After the metal paste has been filled, the metal paste is cured, for example, by performing cold curing, thermal curing, or UV curing. By this step, the reflective layer 5 is formed so as to cover the scintillator layer 3 with the first protective layer 4 interposed therebetween.

Subsequently, the second protective layer 6 is formed on the reflective layer 5. More specifically, in this step, the second protective layer 6 is formed on the reflective layer 5 to cover the scintillator layer 3, the first protective layer 4, and the reflective layer 5 as a whole. Accordingly, it is possible to protect the reflective layer 5 and to improve moisture resistance of the scintillator layer 3. Through the above-mentioned steps, the scintillator panel 1 is manufactured.

The metal paste can be manufactured, for example, as follows. That is, first, a metal powder (such as metal foils), an organic solvent, and a pulverization aid are mixed using a ball mill (a spread pulverization step). Subsequently, the mixture is sieved with a sieve (a sieving step). Through this step, metal particles 8 of which the average size has been controlled are obtained. Subsequently, the mixture is separated into a solid (the metal particles 8) and a liquid (a filtration step). Then, the metal particles 8, an organic solvent, and a binder resin are mixed. As a result, the metal paste is manufactured.

Figure 3:
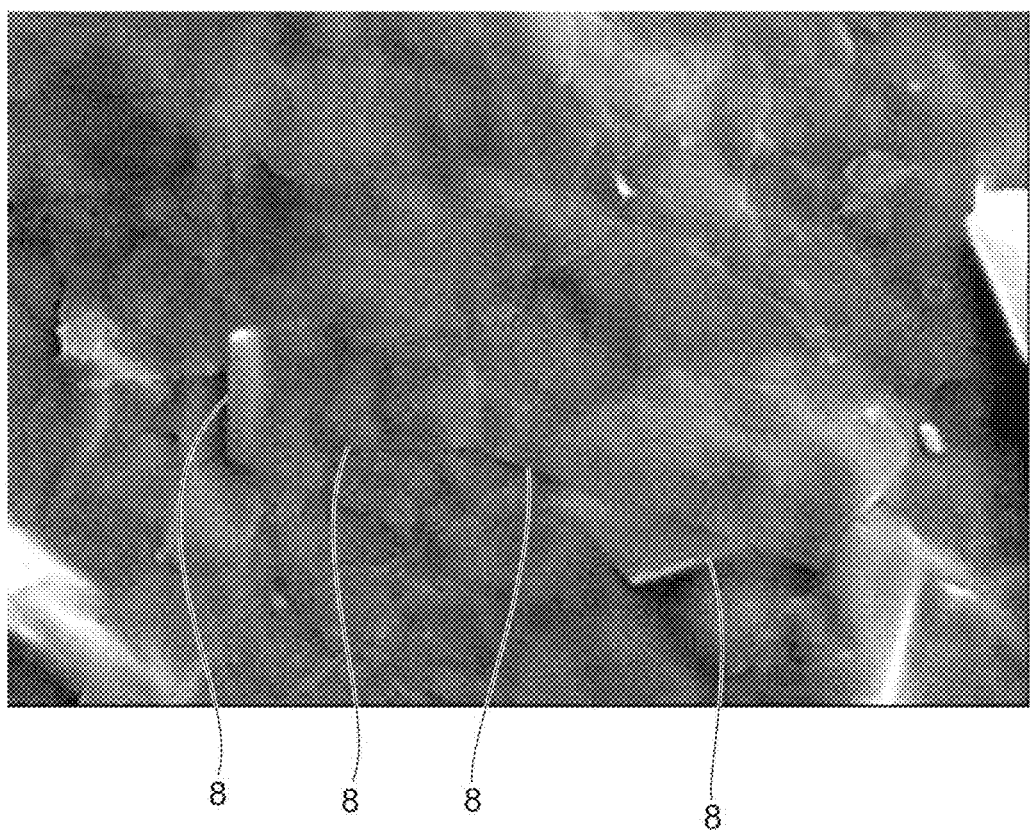
FIG. 3 is a photograph illustrating an example of a reflective layer of the scintillator panel illustrated in FIG. 1.

Advantages which are achieved by the scintillator panel 1 will be described below with reference to FIGS. 1 to 4. FIG. 3 is a photograph illustrating an example of the reflective layer of the scintillator panel illustrated in FIG. 1. In the scintillator panel 1, the scintillator layer 3 includes a plurality of scintillator portions 7 which are arranged with a predetermined pitch on the principal surface 2s of the substrate 2. The reflective layer 5 that reflects scintillation light is provided so as to cover at least the side faces 7s of the scintillator portions 7. The reflective layer 5 includes a plurality of foil-shaped metal particles 8 that extend along the side faces 7s of the scintillator portions 7.

For example, when an absorber layer (for example, an absorber layer including carbon black) that absorbs scintillation light is formed on the scintillator layer 3, an improvement of a resolution is expected but a light output may decrease in comparison with a case in which the absorber layer is not formed. On the other hand, with the scintillator panel 1, it is possible to curb a decrease in a light output and to improve a resolution by using the reflective layer 5 including the foil-shaped metal particles 8. This is because the surface (the side faces 7s and the top faces 70 of the scintillator layer 3 can be covered with a plurality of metal particles 8 as a whole with no break (that is, a continuous reflective surface can be formed) by causing the foil-shaped metal particles 8 that reflect scintillation light to at least partially overlap, as illustrated in FIGS. 2 and 3.

For example, when a reflective layer including spherical metal particles is formed, an improvement in a resolution may not be expected. The reason thereof is considered as follows. That is, it is difficult to cover the side faces 7s in a fine gap between the side faces 7s of the scintillator portions 7 with the spherical metal particles with no break. Accordingly, it is difficult to prevent transmission of scintillation light and to reduce crosstalk.

Figure 4:
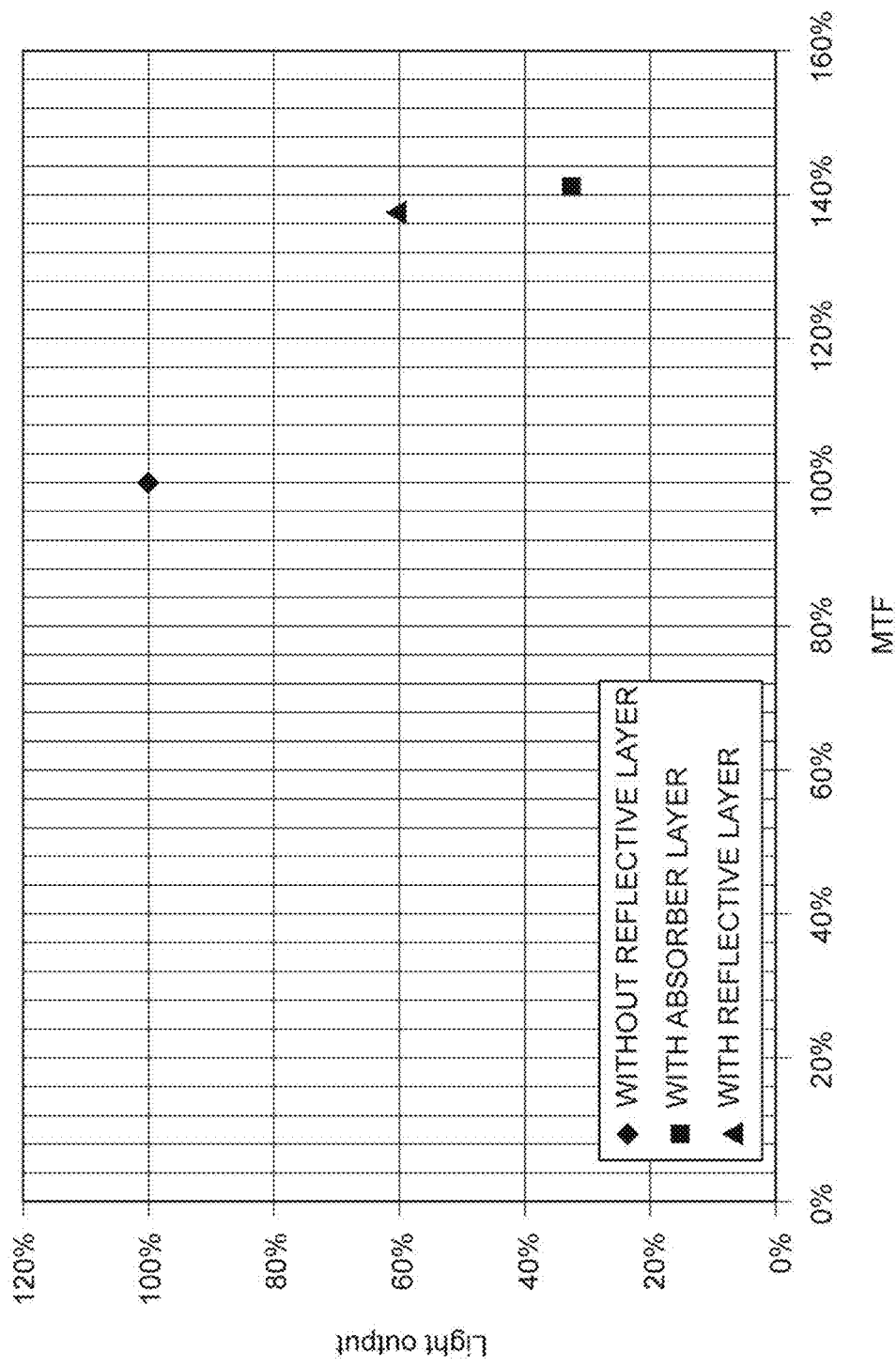
FIG. 4 is a graph illustrating an evaluation result of a resolution and a light output of the scintillator panel.

FIG. 4 is a graph illustrating an evaluation result of a resolution (MTF) and a light output of the scintillator panel. In the graph illustrated in FIG. 4, "WITH REFLECTIVE LAYER" corresponds to an example of the scintillator panel 1. In the example of the scintillator panel 1, CsI:Tl is used as the scintillation material of the scintillator layer 3, the thickness of the scintillator layer 3 (the height H of the scintillator portions 7) is set to 150 µm, the processing depth of the scintillator layer 3 (the depth of the gap between the scintillator portions 7) is set to 150 µm, and the metal particles 8 of the reflective layer 5 are formed of Al.

"WITH ABSORBER LAYER" in the graph illustrated in FIG. 4 corresponds to a scintillator panel according to a first comparative example. In the first comparative example, an absorber layer including carbon is provided instead of the reflective layer 5. "WITHOUT ABSORBER LAYER" in the graph illustrated in FIG. 4 corresponds to a scintillator panel according to a second comparative example. In the second comparative example, the reflective layer 5 and the absorber layer are not provided. In the graph illustrated in FIG. 4, values of resolutions and light outputs in the example and the first comparative example are illustrated relative to the values of the resolution and the light output (100%) in the second comparative example.

As illustrated in FIG. 4, according to the first comparative example of "WITH ABSORBER LAYER," the resolution is improved to 140% in comparison with the second comparative example of "WITHOUT REFLECTIVE LAYER," but the light output is decreased to 30%. On the other hand, according to the example, the resolution is improved to substantially the same degree as in the first comparative example in comparison with the second comparative example and the decrease of the light output is curbed in comparison with the first comparative example. From this evaluation result, it can be seen that the scintillator panel 1 can curb a decrease of a light output and improve a resolution.

Advantages which are achieved by the scintillator panel 1 will be described below. In the scintillator panel 1, the average size of the metal particles 8 is equal to or less than half the gap G between the side faces 7s of the neighboring scintillator portions 7. Accordingly, when the reflective layer 5 is formed, the metal particles 8 can be disposed so as to cover the side faces 7s of the scintillator portions 7 by easily and reliably entering the foil-shaped metal particles 8 to the gaps between the side faces 7s of the scintillator portions 7. Accordingly, it is possible to reliably curb a decrease in a light output and to further improve a resolution.

In the scintillator panel 1, the first protective layer 4 is formed on the scintillator layer 3. Accordingly, when the reflective layer 5 is formed, it is possible to prevent an organic solvent included in the metal paste from entering between the columnar crystals of the scintillator portions 7. Since the scintillator layer 3 does not come in direct contact with the metal particles 8, it is possible to prevent a reaction between the scintillator material and the metal from giving an adverse influence.

An example of the scintillator panel according to an aspect of the invention has been described above. Accordingly, a scintillator panel according to an aspect of the invention is not limited to the scintillator panel 1. As the scintillator panel according to an aspect of the invention, the scintillator panel 1 can be arbitrarily modified or can be applied to another device without departing from the gist of the appended claims.

Figure 5:
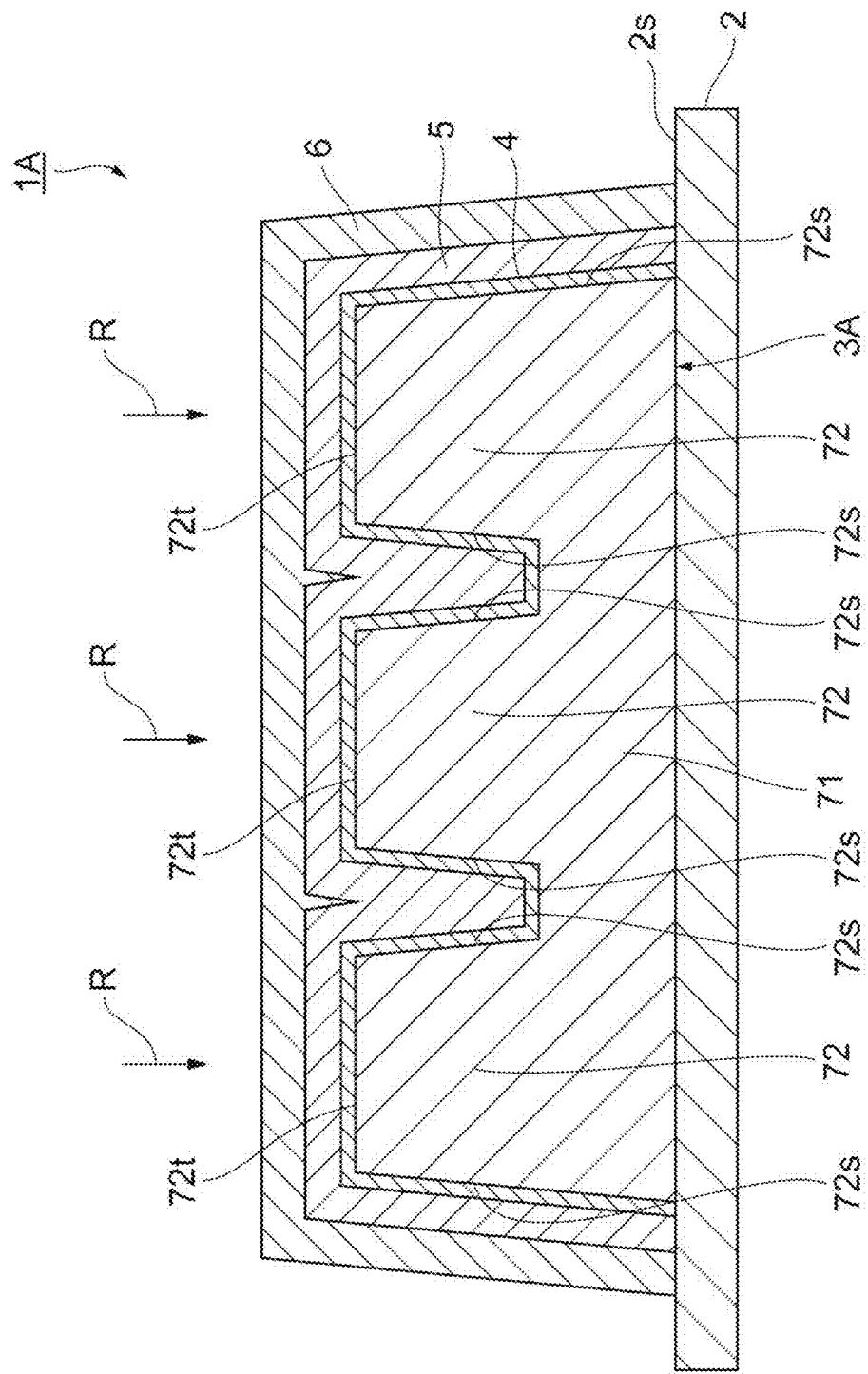
FIG. 5 is a sectional view of a scintillator panel according to a modified example.

FIG. 5 is a sectional view of a scintillator panel according to a modified example. As illustrated in FIG. 5, a scintillator panel 1A is different from the scintillator panel 1 in that a scintillator layer 3A is provided instead of the scintillator layer 3. The scintillator layer 3A generates scintillation light such as visible light in response to incidence of radiation R such as X-rays. The scintillator layer 3A is formed on the principal surface 2s of the substrate 2. For example, the scintillator layer 3A is formed in a rectangular area of the principal surface 2s when viewed in a direction crossing (for example, perpendicular to) the principal surface 2s.

The scintillator layer 3A includes a single base portion 71 and a plurality of scintillator portions 72. The base portion 71 and the scintillator portions 72 are formed of, for example, a single crystal of a scintillation material. Alternatively, the base portion 71 and the scintillator portions 72 are formed of, for example, a plurality of columnar crystals of a scintillation material. The scintillation material is the same as described above.

The base portion 71 is formed on the principal surface 2s. The base portion 71 extends along the principal surface 2s. For example, the base portion 71 comes in contact with the principal surface 2s. The scintillator portions 72 are two-dimensionally arranged on the principal surface 2s and the base portion 71. The scintillator portions 72 are not directly connected to each other. In other words, the scintillator portions 72 are formed, for example, in pixel units of an imaging sensor (that is, the scintillator layer 3A is partitioned into pixels). The scintillator portions 72 are connected to each other via the base portion 71. In other words, the base portion 71 connects the scintillator portions 72.

A sectional shape of each scintillator portion 72 is, for example, a trapezoidal shape that reduces away from the principal surface 2s and the base portion 71. That is, each scintillator portion 72 is a taper shape in which a sectional area increases from the opposite side of the principal surface 2s and the base portion 71 to the principal surface 2s and the base portion 71. Each scintillator portion 72 includes side faces 72s that extend in a direction crossing the principal surface 2s (for example, a direction in which columnar crystals grow). Each scintillator portion 72 includes a top face 72t that extends in a direction parallel to the principal surface 2s. The top face 72t connects the side faces 72s.

A relationship between the sizes of parts of the scintillator layer 3A and the average size of the metal particles 8 can be defined in the same range as in the scintillator panel 1. For example, the thickness of the scintillator layer 3A (the sum of the height of the base portion 71 and the height of the scintillator portions 72) can be set to about 600 µm. The processing depth of the scintillator layer 3A (the depth of the gaps between the scintillator portions 72) can be set to, for example, 300 µm. In this case, the height of the base portion 71 and the height of the scintillator portions 72 are both about 300 µm.

Such a scintillator layer 3A can be manufactured, for example, by forming grooves in the scintillator layer with a processing depth not reaching the principal surface 2s at the time of laser processing of the scintillator layer in the method of manufacturing the scintillator panel 1. With the scintillator panel 1A, the same advantages as in the scintillator panel 1 can be achieved.

Figure 6:
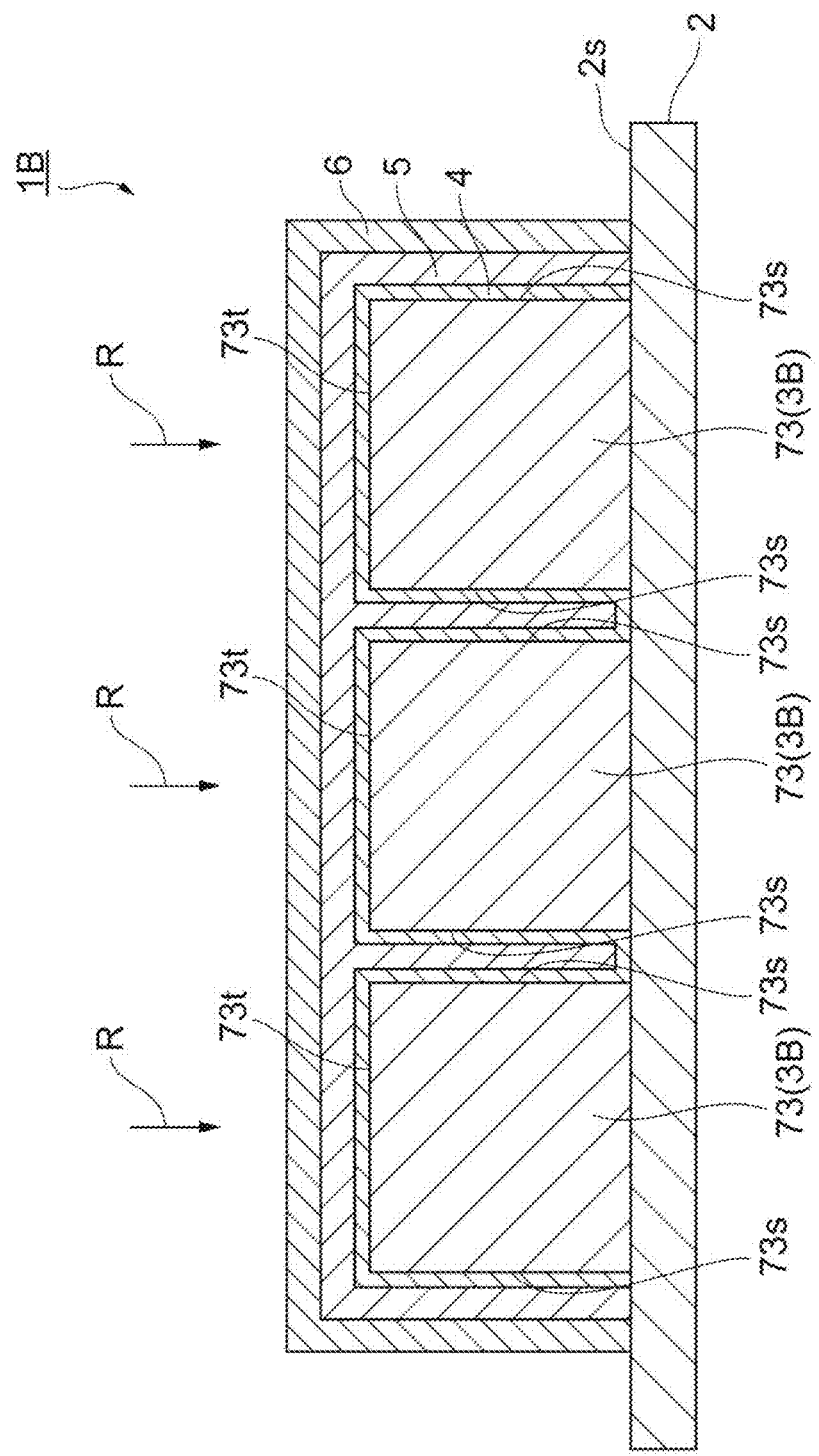
FIG. 6 is a sectional view of a scintillator panel according to another modified example.

FIG. 6 is a sectional view of a scintillator panel according to another modified example. As illustrated in FIG. 6, a scintillator panel 1B is different from the scintillator panel 1 in that a scintillator layer 3B is provided instead of the scintillator layer 3. The scintillator layer 3B generates scintillation light such as visible light in response to incidence of radiation R such as X-rays. The scintillator layer 3B is formed on the principal surface 2s of the substrate 2. For example, the scintillator layer 3B is formed in a rectangular area of the principal surface 2s when viewed in a direction crossing (for example, perpendicular to) the principal surface 2s.

The scintillator layer 3B includes a plurality of scintillator portions 73. The scintillator portions 73 are formed of, for example, a single crystal of a scintillation material. Alternatively, the scintillator portions 73 are formed of, for example, a plurality of columnar crystals of a scintillation material. The scintillation material is the same as described above. The scintillator portions 73 are two-dimensionally arranged with a predetermined pitch on the principal surface 2s. The scintillator portions 73 are not connected to each other. In other words, the scintillator portions 73 are formed, for example, in pixel units of an imaging sensor (that is, the scintillator layer 3A is partitioned into pixels).

A sectional shape of each scintillator portion 73 is a rectangular shape. That is, the scintillator portions 73 do not substantially have taper shapes in comparison with the scintillator portions 7. Each scintillator portion 73 includes side faces 73s that extend in a direction crossing the principal surface 2s (for example, a direction in which columnar crystals grow). Each scintillator portion 73 includes a top face 73t that extends in a direction parallel to the principal surface 2s. The top face 73t connects the side faces 73s. The side faces 73s which are arranged along one of two-dimensional arrangement directions of the scintillator portions 73 are substantially parallel to each other.

A relationship between the sizes of parts of the scintillator layer 3B and the average size of the metal particles 8 can be defined in the same range as in the scintillator panel 1. In the scintillator layer 3B, since the neighboring side faces 73s in one direction are substantially parallel to each other, the gap G between the side faces 73s is substantially constant in a direction from the top face 73t to the principal surface 2s. In the scintillator panel 1B, the first protective layer 4, the reflective layer 5, and the second protective layer 6 are formed to follow the rectangular shapes of the scintillator portions 73.

Such a scintillator layer 3B can be manufactured, for example, by controlling processing conditions and the like such that the rectangular scintillator portions 73 are formed at the time of laser processing of the scintillator layer in the method of manufacturing the scintillator panel 1. With the scintillator panel 1B, the same advantages as in the scintillator panel 1 can be achieved.

In the scintillator panel 1A illustrated in FIG. 5, the sectional shape of each scintillator portion 72 may be set to a rectangular shape.

In the above-mentioned embodiment, an example in which an aspect of the invention is applied to a scintillator panel (for example, the scintillator panels 1, 1A, and 1B) has been described. In such scintillator panels, a sensor panel (for example, a TFT panel or a CMOS image sensor panel) including photoelectric conversion elements can be used as a substrate to construct a radiation detector. A radiation detector according to an embodiment will be described below.

Figure 7:
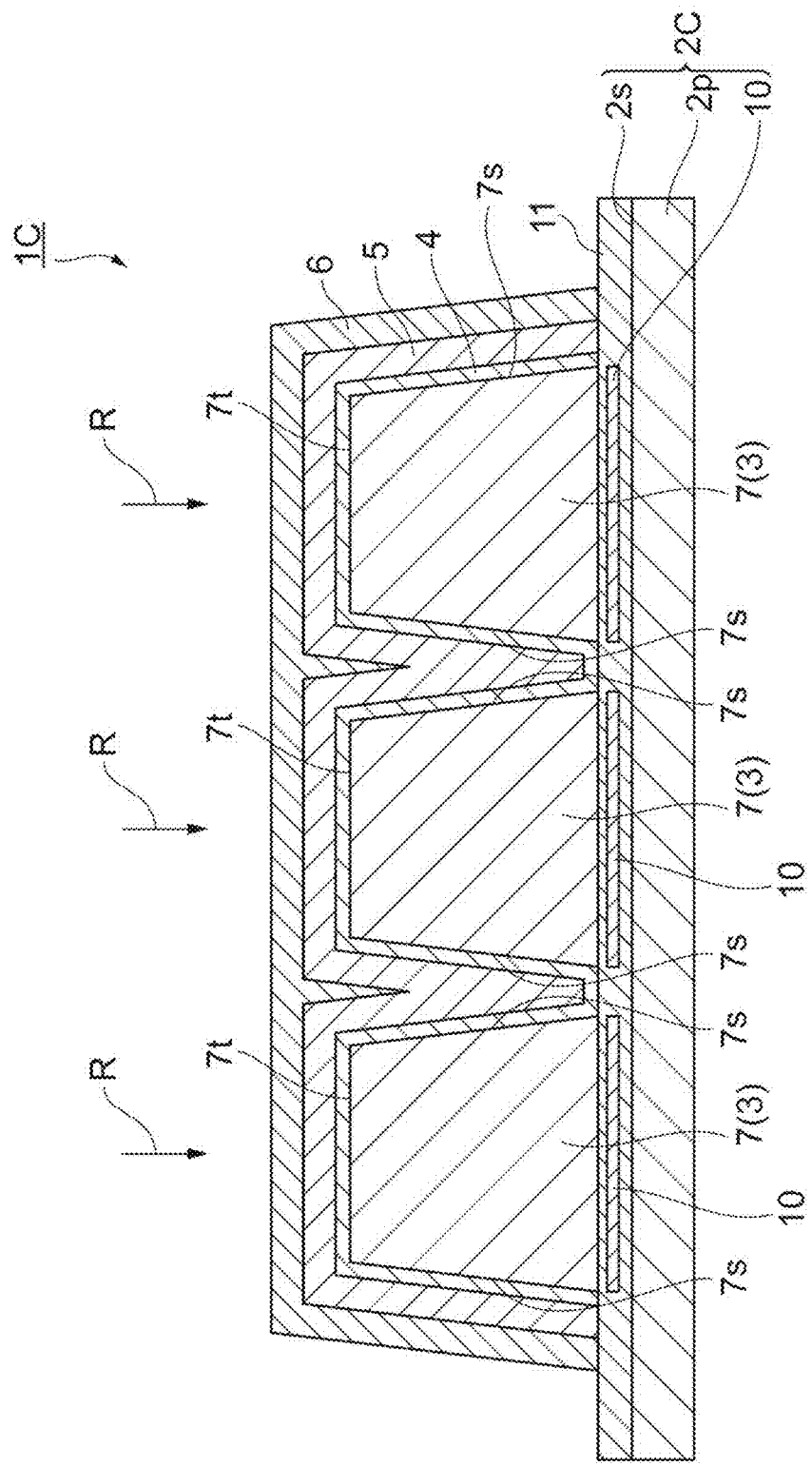
FIG. 7 is a sectional view of a radiation detector according to the embodiment.

FIG. 7 is a sectional view of a radiation detector according to the embodiment. As illustrated in FIG. 7, a radiation detector 1C is different from the scintillator panel 1 in that a substrate 2C serving as a sensor panel is provided instead of the substrate 2. The substrate (the sensor panel) 2C includes a principal surface 2s and a plurality of photoelectric conversion elements 10 formed on the principal surface 2s. More specifically, the substrate 2C includes a panel-shaped base portion 2p including the principal surface 2s. The photoelectric conversion elements 10 are arranged two-dimensionally on the principal surface 2s.

A scintillator layer 3 is formed on the principal surface 2s and the photoelectric conversion elements 10, for example, by vapor deposition. Here, a film portion 11 such as a passivation film or a planarization film is formed on the principal surface 2s and the photoelectric conversion elements 10. The scintillator layer 3 is formed on the principal surface 2s and the photoelectric conversion elements 10 with the film portion 11 interposed therebetween. The scintillator layer 3 is optically coupled to the photoelectric conversion elements 10. More specifically, in the scintillator layer 3, one scintillator portion 7 is provided so as to correspond to one photoelectric conversion element 10. That is, the scintillator portions 7 are two-dimensionally arranged such that they are located on the photoelectric conversion elements 10 when viewed in a direction crossing the principal surface 2s. Accordingly, the scintillator portions 7 are arranged with a pixel pitch of the photoelectric conversion elements 10. Accordingly, the scintillator portions 7 are optically coupled to the photoelectric conversion elements 10 respectively.

Accordingly, the photoelectric conversion elements 10 receive scintillation light which is generated from the scintillator layer 3 (the respective scintillator portions 7) in response to incidence of radiation R and output an electrical signal corresponding to the scintillation light. The electrical signal is externally extracted by a wire or the like which is not illustrated. Accordingly, the radiation detector 1C detects radiation R.

The radiation detector 1C achieves at least the same advantages as in the above-mentioned scintillator panel. More specifically, in the radiation detector 1C, the scintillator layer 3 includes a plurality of scintillator portions 7 which are arranged with the pixel pitch of the photoelectric conversion elements 10 on the substrate 2C. A reflective layer 5 that reflects scintillation light is disposed so as to cover at least the side faces 7s of the scintillator portions 7. The reflective layer 5 includes a plurality of foil-shaped metal particles 8 that extend along the side faces 7s of the scintillator portions 7. In this way, by using the reflective layer 5 including the foil-shaped metal particles 8, it is possible to curb a decrease in a light output and to improve a resolution.

In the radiation detector 1C, the average size of the metal particles 8 is equal to or less than half the gap G between the side faces 7s of the neighboring scintillator portions 7. Accordingly, when the reflective layer 5 is formed, the foil-shaped metal particles 8 can easily and satisfactorily enter the gaps between the side faces 7s of the scintillator portions 7 and the metal particles 8 can be arranged to cover the side faces 7s of the scintillator portions 7. Accordingly, it is possible to satisfactorily curb a decrease in a light output and to further improve a resolution.

In the radiation detector 1C, a first protective layer 4 is formed on the scintillator layer 3. Accordingly, when the reflective layer 5 is formed, it is possible to prevent an organic solvent included in a metal paste from invading between the columnar crystals of the scintillator portions 7. Since the scintillator layer 3 and the metal particles 8 do not come into direct contact with each other, it is possible to prevent a reaction between the scintillation material and metal from giving an adverse influence.

The radiation detector 1C can achieve the following different advantages. That is, the radiation detector 1C is constructed by forming the scintillator layer 3 directly on the substrate 2C (and the film portion 11) serving as a sensor panel, for example, by vapor deposition. Accordingly, when the radiation detector is constructed, it is not necessary to bond a sensor panel and a scintillator panel, which are prepared as independent members, to each other. In the scintillator panels 1, 1A, and 1B, a sensor panel may be separately provided on the rear surface of the substrate 2 opposite to the principal surface 2s to construct a radiation detector.

In the above description, the radiation detector 1C is constructed by replacing the substrate 2 of the scintillator panel 1 with the substrate 2C including the photoelectric conversion elements 10. However, the substrate 2 of the scintillator panels 1A and 1B may be replaced with the substrate 2C including the photoelectric conversion elements 10 to construct a radiation detector.

INDUSTRIAL APPLICABILITY

It is possible to provide a scintillator panel and a radiation detector that can curb a decrease of a light output and improve a resolution.

REFERENCE SIGNS LIST 1, 1A, 1B . . . scintillator panel, 1C . . . radiation detector, 2, 2C . . . substrate, 2s . . . principal surface, 3, 3A, 3B . . . scintillator layer, 5 . . . reflective layer, 7, 72, 73 . . . scintillator portion, 7s, 72s, 73s . . . side face, 8 . . . metal particle, 10 . . . photoelectric conversion element, G . . . gap, R . . . radiation

The invention claimed is:

1. A scintillator panel that converts radiation into scintillation light, the scintillator panel comprising:
   a substrate that includes a principal surface;
   a scintillator layer that is disposed on the principal surface; and
   a reflective layer that is disposed on the scintillator layer and reflects the scintillation light,
   wherein the scintillator layer includes a plurality of scintillator portions which are arranged with a predetermined pitch on the principal surface,
   wherein each scintillator portion includes a side face that extends in a direction crossing the principal surface, and
   wherein the reflective layer includes a plurality of metal particles, each metal particle having a foil shape extending along the side face and overlapping with another metal particle so as to cover the side face.

2. The scintillator panel according to claim 1, wherein an average size of the metal particles is equal to or less than half a gap size between the side faces of the neighboring scintillator portions.

3. The scintillator panel according to claim 1, wherein the scintillator layer is formed of a scintillator material containing CsI as a main component.

4. The scintillator panel according to claim 1, wherein the scintillator layer is formed of a scintillator material which is GOS.

5. The scintillator panel according to claim 1, wherein each scintillator portion is formed of a single crystal of a scintillator material.

6. The scintillator panel according to claim 1, wherein each scintillator portion is formed of a plurality of columnar crystals of a scintillator material.

7. A radiation detector comprising:
   a substrate that includes a principal surface and a plurality of photoelectric conversion elements formed on the principal surface;
   a scintillator layer that is disposed on the plurality of photoelectric conversion elements and converts radiation into scintillation light; and
   a reflective layer that is disposed on the scintillator layer and reflects the scintillation light,
   wherein the scintillator layer includes a plurality of scintillator portions which are arranged with a pixel pitch of the photoelectric conversion elements,
   wherein each scintillator portion includes a side face that extends in a direction crossing the principal surface, and
   wherein the reflective layer includes a plurality of metal particles, each metal particle having a foil shape extending along the side face and overlapping with another metal particle so as to cover the side face.

8. The radiation detector according to claim 7, wherein an average size of the metal particles is equal to or less than half a gap size between the side faces of the neighboring scintillator portions.

9. The radiation detector according to claim 7, wherein the scintillator layer is formed of a scintillator material containing CsI as a main component.

10. The radiation detector according to claim 7, wherein the scintillator layer is formed of a scintillator material which is GUS.

11. The radiation detector according to claim 7, wherein each scintillator portion is formed of a single crystal of a scintillator material.

12. The radiation detector according to claim 7, wherein each scintillator portion is formed of a plurality of columnar crystals of a scintillator material.

* * * * *